(12) United States Patent
Hasegawa et al.

(10) Patent No.: US 12,178,951 B2
(45) Date of Patent: Dec. 31, 2024

(54) BLOOD PURIFICATION APPARATUS AND METHOD OF ESTIMATING PATIENT'S STATE OF NUTRITION ON BLOOD PURIFICATION APPARATUS

(71) Applicant: Nikkiso Company Limited, Tokyo (JP)

(72) Inventors: Shinya Hasegawa, Shizuoka (JP); Satoru Kawarabayashi, Tokyo (JP); Masahiro Toyoda, Shizuoka (JP); Kunihiko Akita, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 635 days.

(21) Appl. No.: 17/104,626

(22) Filed: Nov. 25, 2020

(65) Prior Publication Data

US 2021/0077704 A1 Mar. 18, 2021

Related U.S. Application Data

(63) Continuation of application No. PCT/JP2019/024334, filed on Jun. 19, 2019.

(30) Foreign Application Priority Data

Jun. 20, 2018 (JP) .................................. 2018-116787

(51) Int. Cl.
*A61M 1/36* (2006.01)
*A61B 5/00* (2006.01)
(Continued)

(52) U.S. Cl.
CPC ......... *A61M 1/3601* (2014.02); *A61B 5/6866* (2013.01); *A61M 1/16* (2013.01);
(Continued)

(58) Field of Classification Search
CPC ..... A61B 5/6866; A61M 1/16; A61M 1/3413; A61M 1/3441; A61M 1/3601;
(Continued)

(56) References Cited

U.S. PATENT DOCUMENTS

| 4,640,445 A | 2/1987 | Yamada |
| 7,758,532 B2 | 7/2010 | Mori et al. |

(Continued)

FOREIGN PATENT DOCUMENTS

| JP | H06-218047 A | 8/1994 |
| JP | 2002-126075 A | 5/2002 |

(Continued)

OTHER PUBLICATIONS

International Search Report dated Sep. 10, 2019 for Application No. PCT/JP2019/024334 published as WO2019244942.

(Continued)

*Primary Examiner* — Dirk R Bass
(74) *Attorney, Agent, or Firm* — Young Basile Hanlon & MacFarlane, P.C.

(57) ABSTRACT

A blood purification apparatus that accurately calculates the colloid osmotic pressure of a patient's blood. A dialyzer included in the blood purification apparatus has thereinside blood flow routes and dialysate flow routes that are separated from each other by hollow fibers. An ultrafiltration pump draws out water from the blood in the blood flow routes through the hollow fibers into the dialysate flow routes. Four detecting units measure the pressures of liquid flowing into the blood flow routes, the liquid discharged from the blood flow routes, dialysate flowing into the dialysate flow routes, and the dialysate discharged from the dialysate flow routes. The pressures at the four positions, the transmembrane pressure difference can be calculated. The blood flow routes are filled with a priming solution, and the transmembrane pressure difference (TMPa) is measured. Subsequently, the blood flow routes are filled with the patient's blood, and the transmembrane pressure difference (TMPb) is measured. Referencing TMPa and TMPb, the colloid osmotic pressure of the patient's blood can be (Continued)

calculated. Referencing colloid osmotic pressure, the plasma total protein can be calculated. Referencing plasma total protein, the patient's state of nutrition can be estimated.

14 Claims, 9 Drawing Sheets

(51) Int. Cl.
    *A61M 1/16*         (2006.01)
    *A61M 1/34*         (2006.01)
    *A61M 60/279*      (2021.01)

(52) U.S. Cl.
    CPC ........ *A61M 1/3413* (2013.01); *A61M 1/3643* (2013.01); *A61M 1/3638* (2014.02); *A61M 60/279* (2021.01); *A61M 2205/3331* (2013.01)

(58) Field of Classification Search
    CPC .............. A61M 1/3638; A61M 1/3639; A61M 1/3643; A61M 1/3649; A61M 2205/3331; A61M 2230/20; A61M 60/279
    See application file for complete search history.

(56) References Cited

U.S. PATENT DOCUMENTS

| | | |
|---|---|---|
| 8,795,218 B2 | 8/2014 | Lannoy |
| 2006/0105056 A1* | 5/2006 | Ecanow .................... A61P 7/00 514/1.5 |
| 2014/0305869 A1 | 10/2014 | Wolff et al. |
| 2019/0217001 A1* | 7/2019 | Kawarabayashi .. A61M 1/3458 |
| 2020/0061281 A1* | 2/2020 | Desouza ............. A61M 1/1601 |

FOREIGN PATENT DOCUMENTS

| | | |
|---|---|---|
| JP | 2011-110098 A | 6/2011 |
| JP | 2011-200407 A | 10/2011 |
| JP | 2013-027455 A | 2/2013 |
| WO | 2001/076661 A1 | 10/2001 |
| WO | 2012/042323 A2 | 4/2012 |
| WO | 2018/017623 A1 | 1/2018 |

OTHER PUBLICATIONS

Potentially related U.S. Appl. No. 17/104,621, filed Nov. 25, 2020 entitled "Blood Purification Apparatus and Method of Acquiring Plasma Flow Rate On Blood Purification Apparatus," Published as WO2019244941.

* cited by examiner

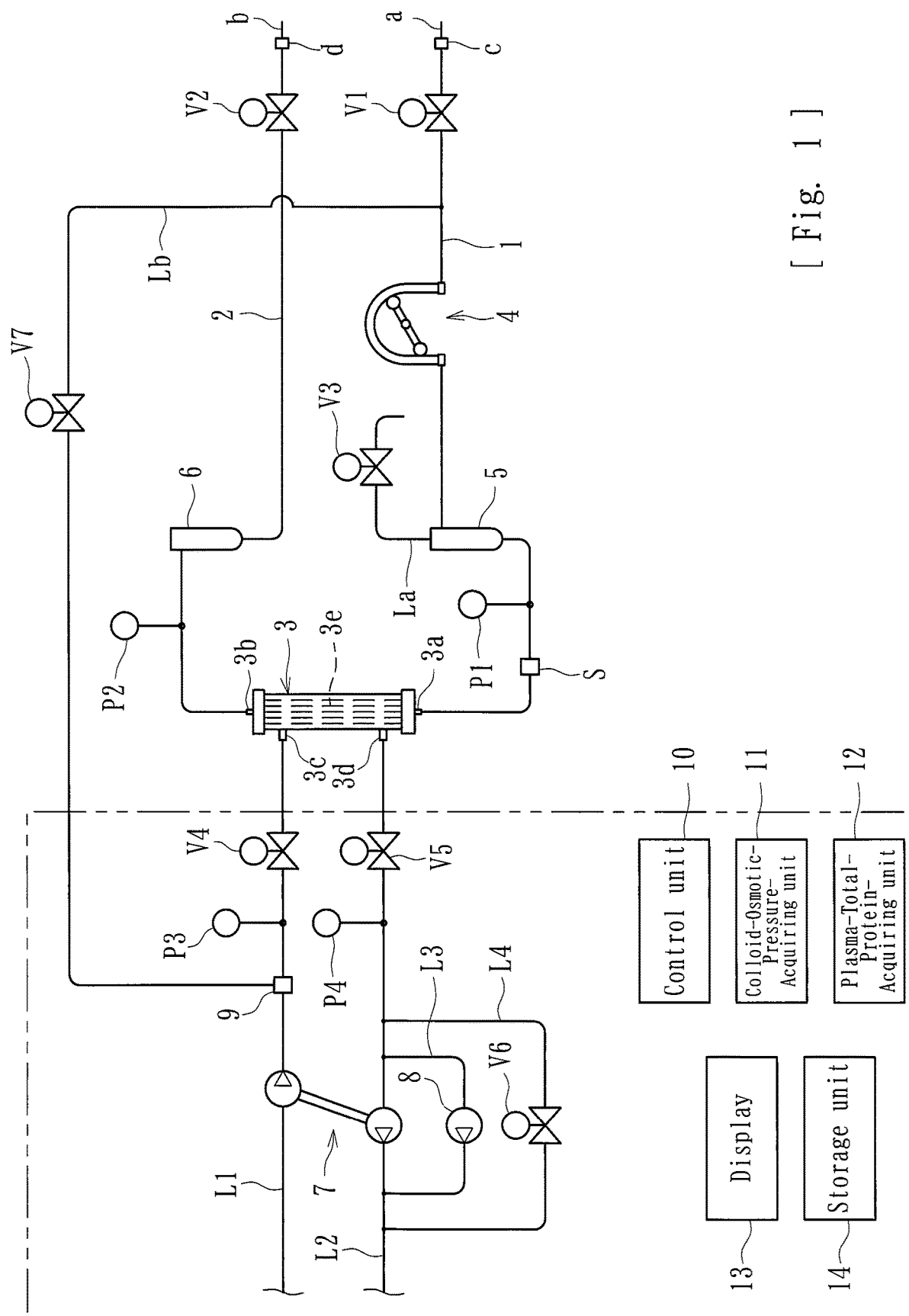
[Fig. 1]

[Fig. 2]
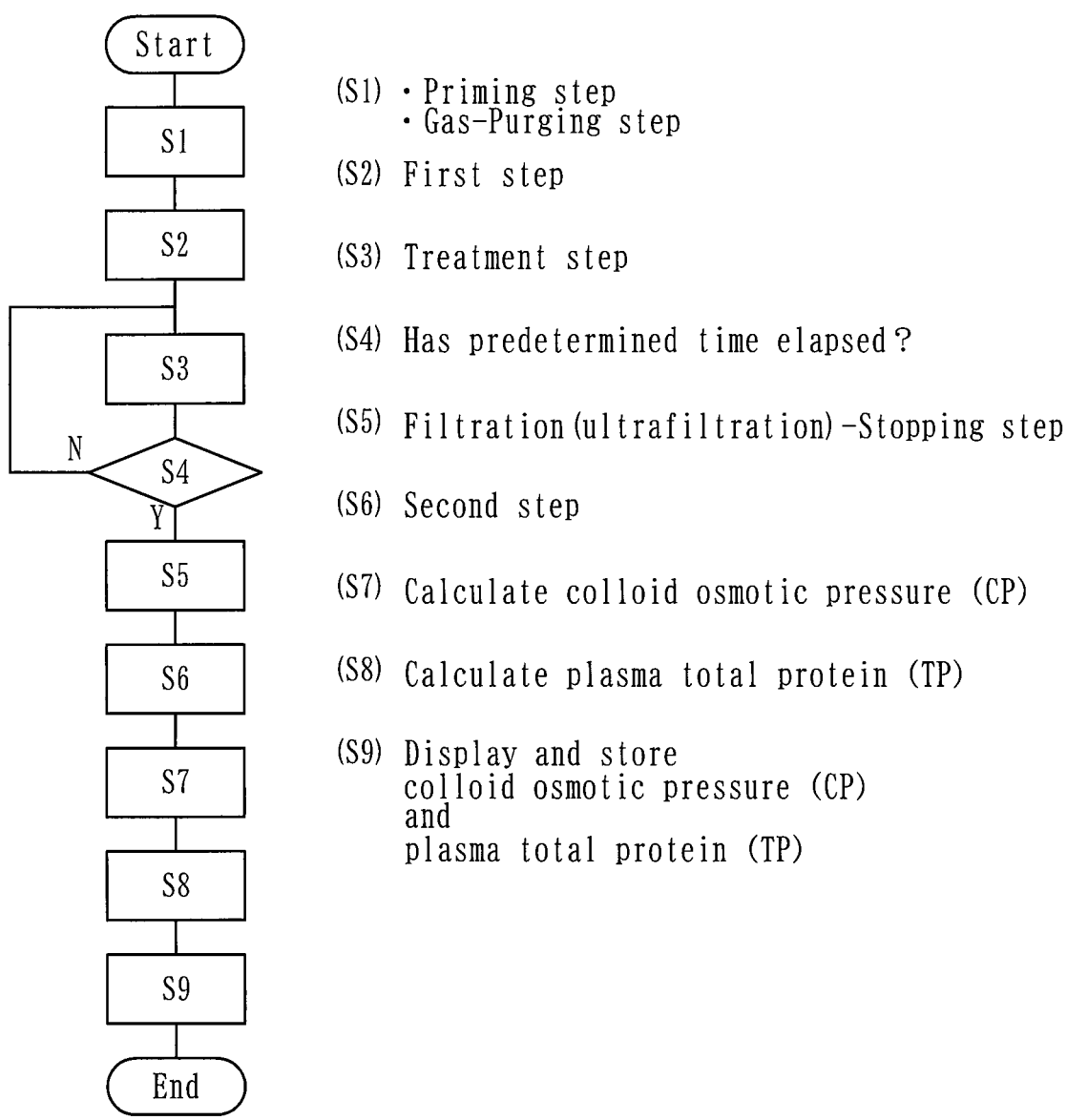

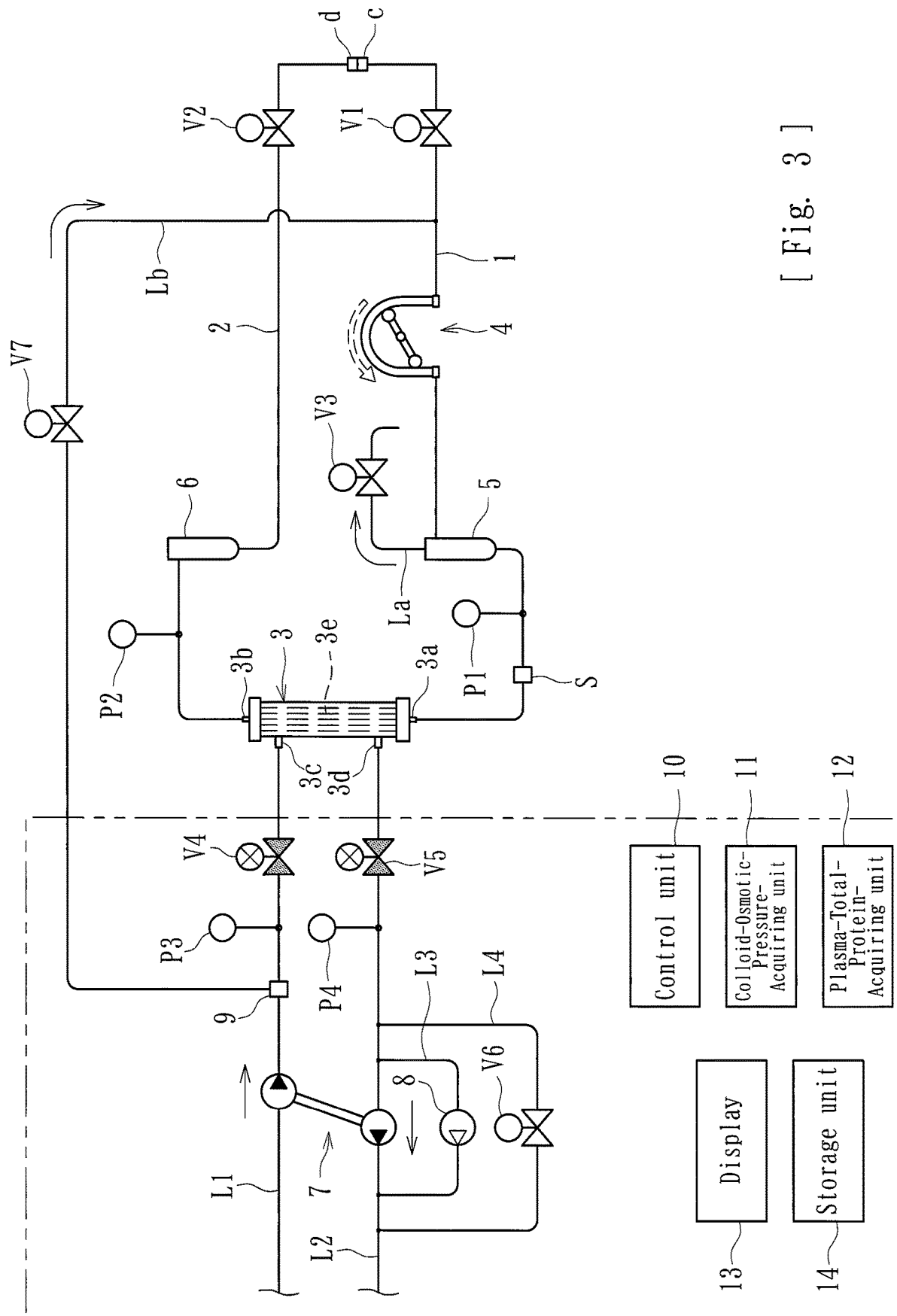
[Fig. 3]

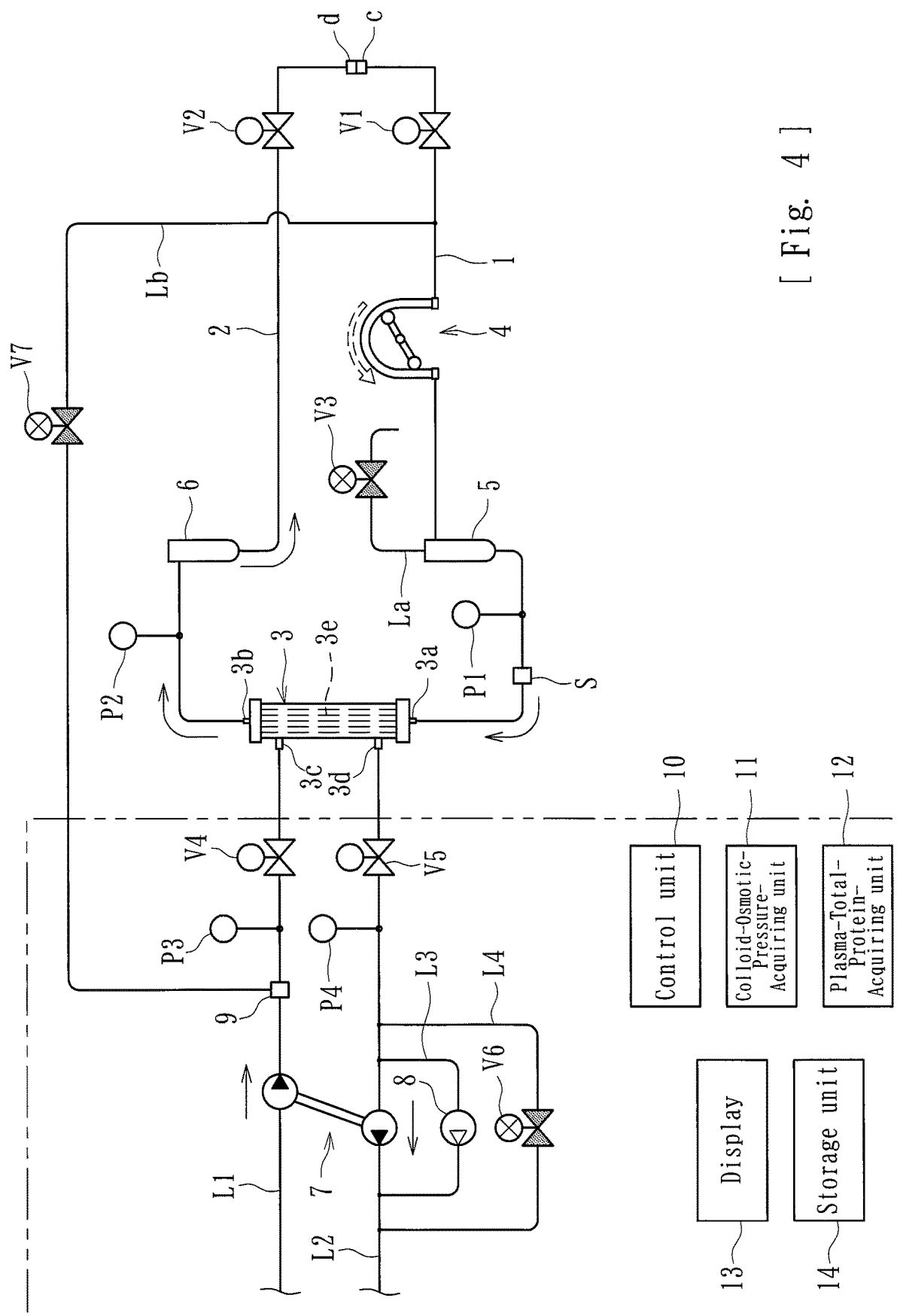
[Fig. 4]

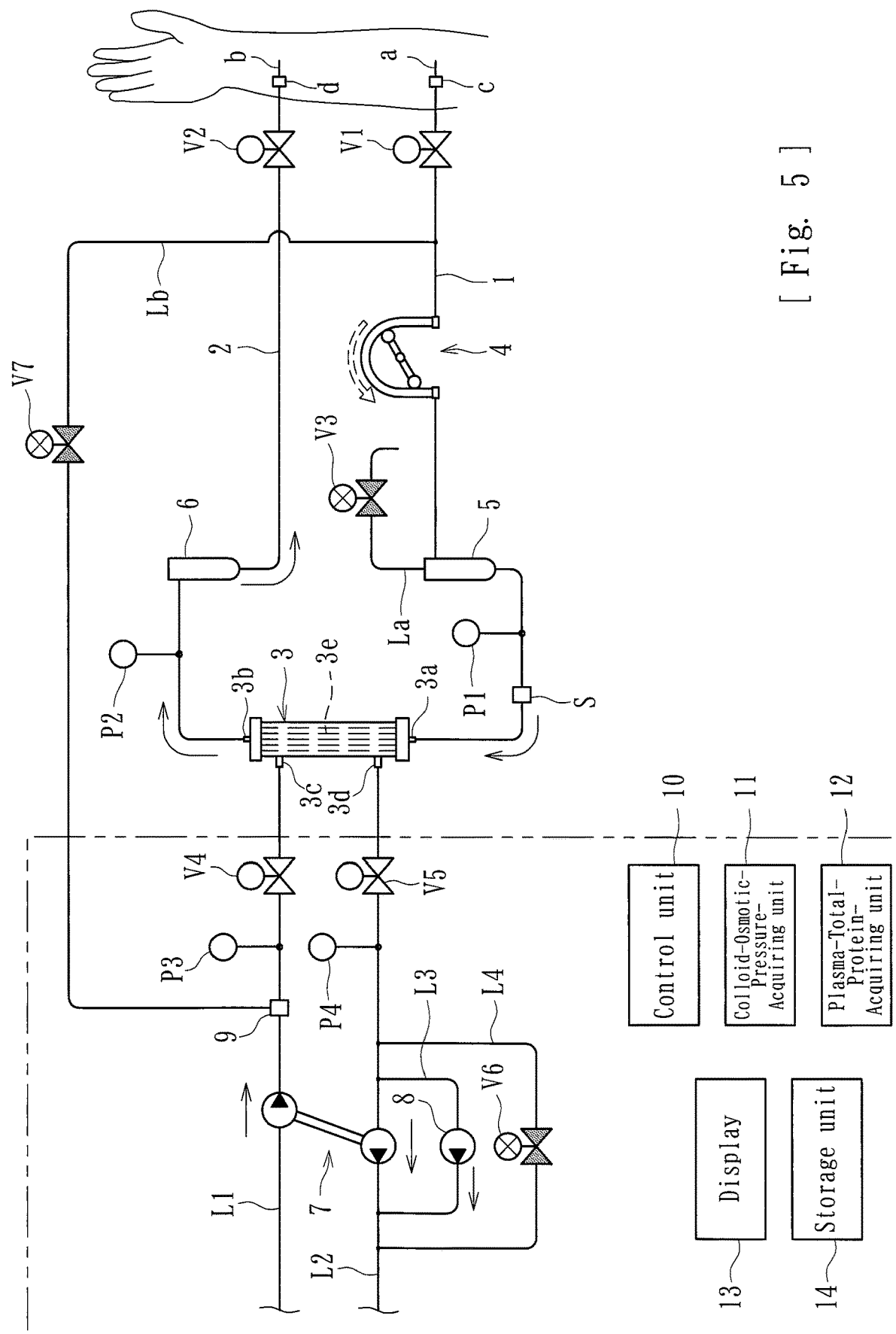
[ Fig. 5 ]

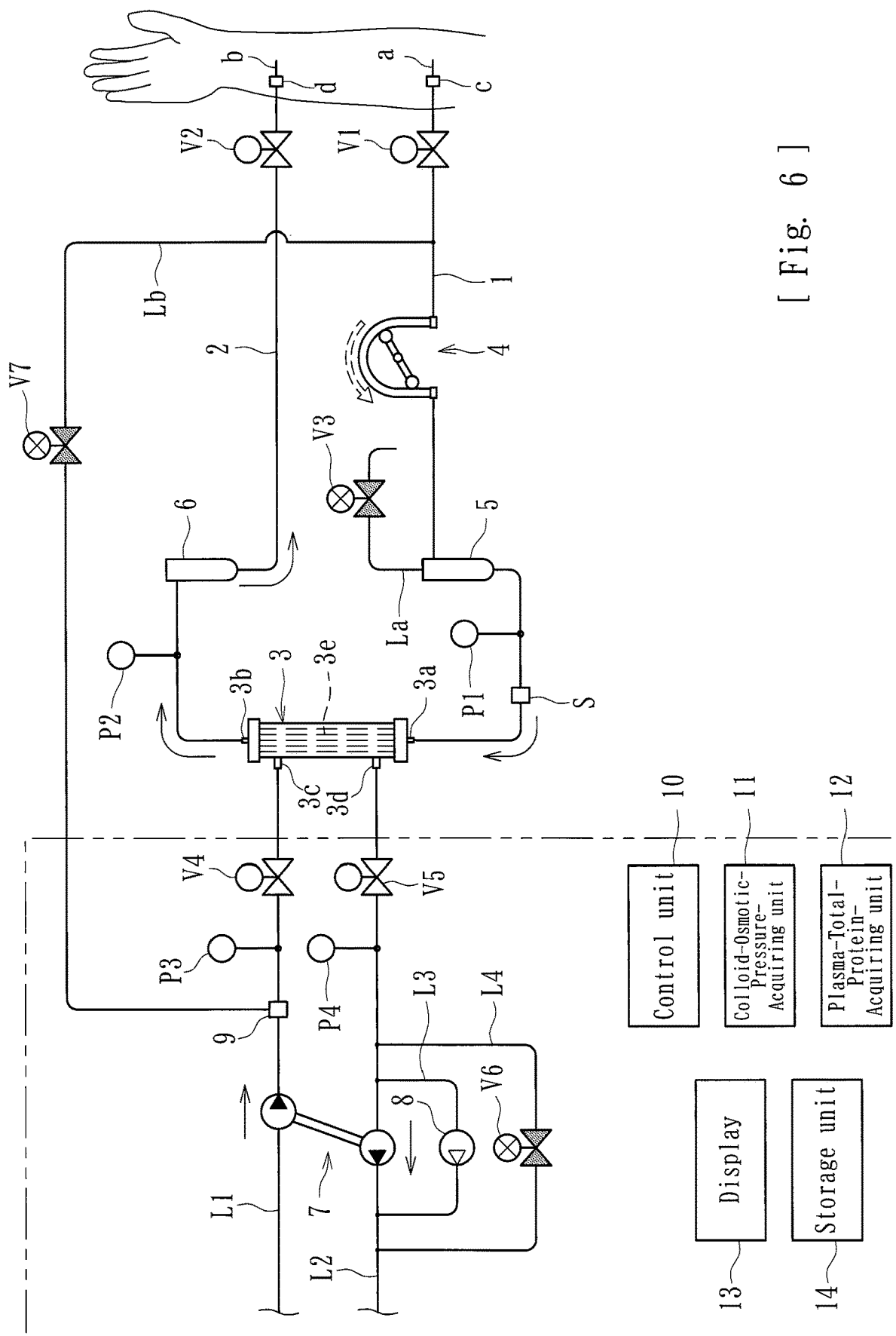
[Fig. 6]

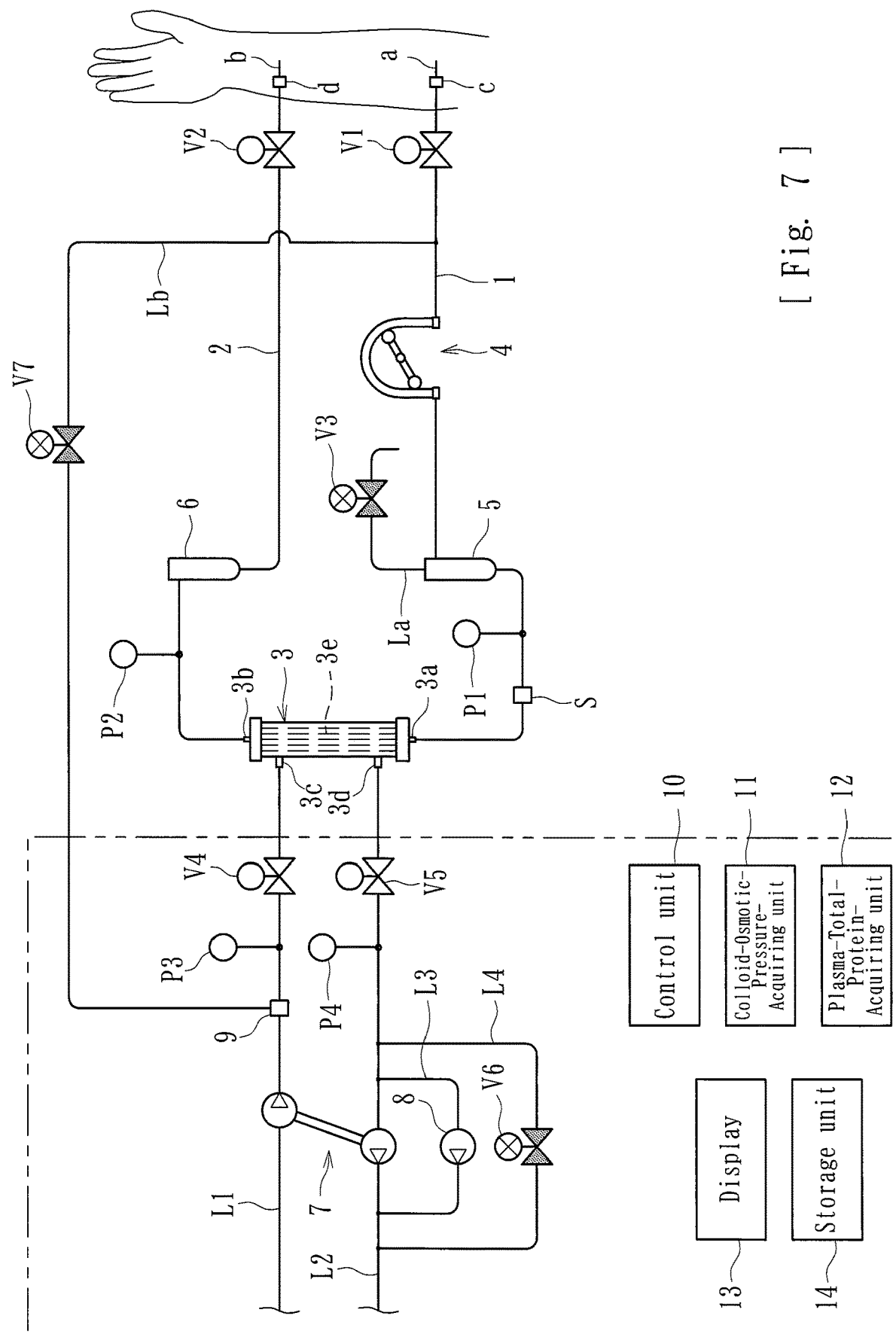
[Fig. 7]

[Fig. 8]
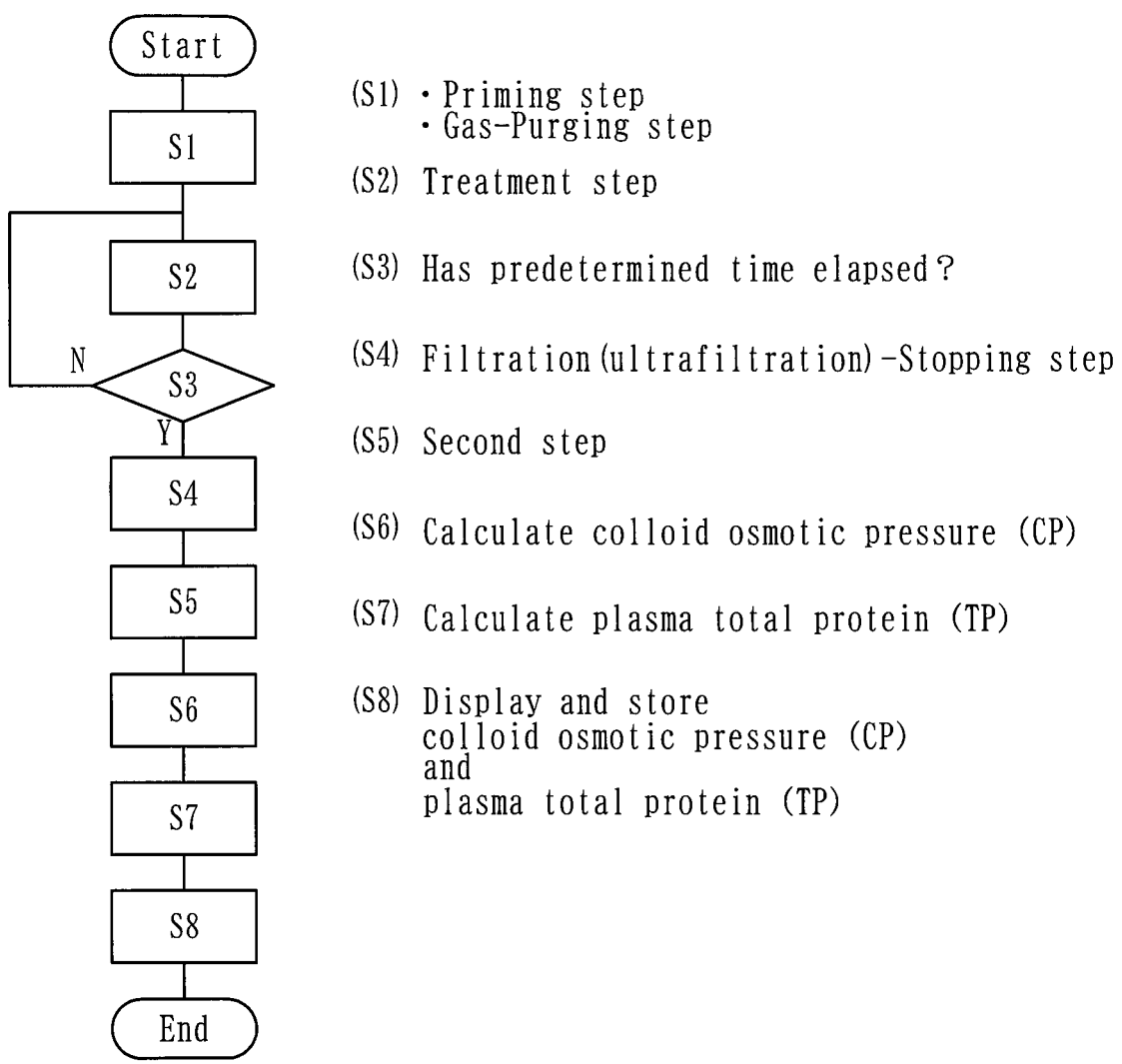

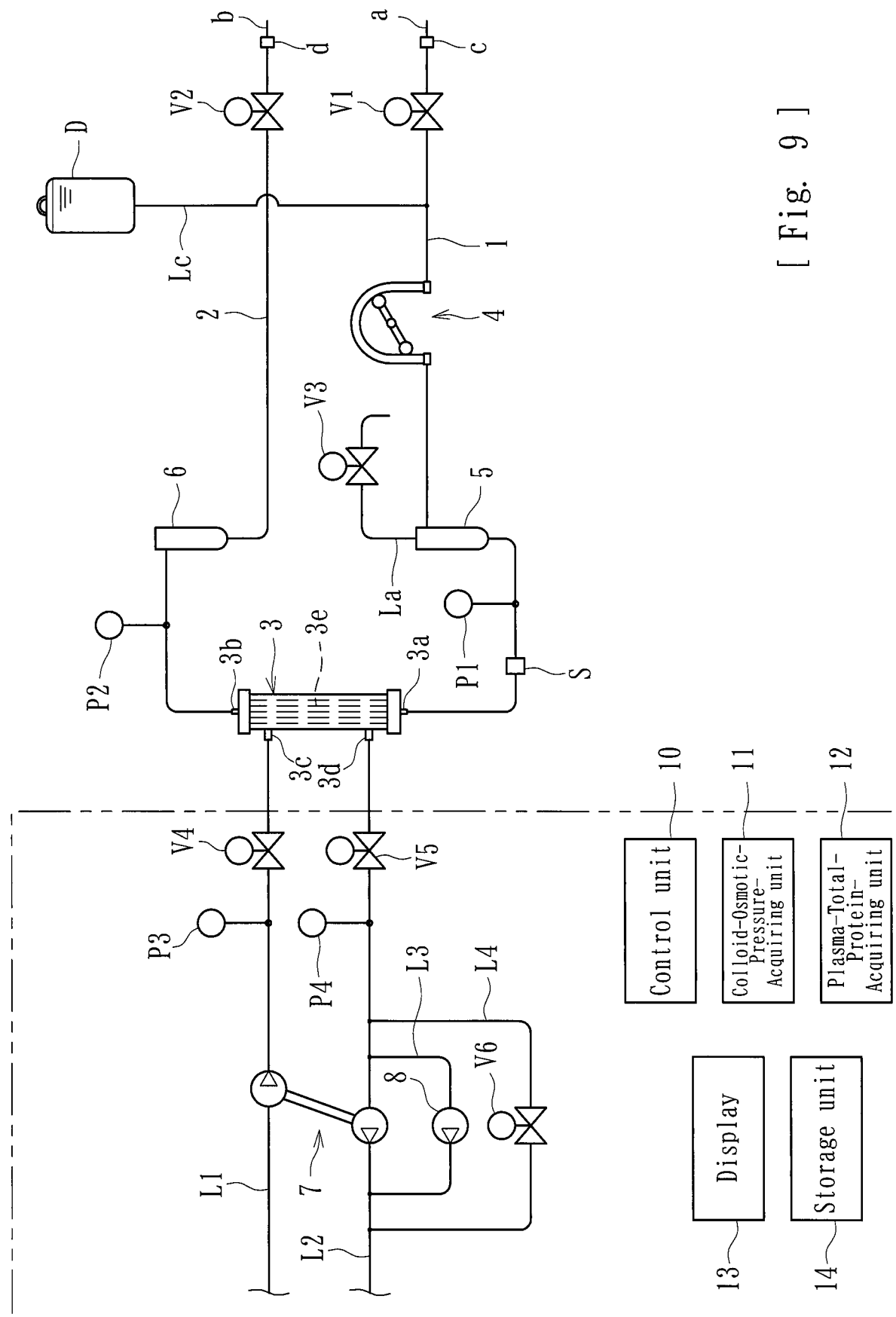
[Fig. 9]

BLOOD PURIFICATION APPARATUS AND METHOD OF ESTIMATING PATIENT'S STATE OF NUTRITION ON BLOOD PURIFICATION APPARATUS

CROSS-REFERENCE TO RELATED APPLICATION(S)

This application is a continuation of International Application No. PCT/JP2019/024334, filed on Jun. 19, 2019, which claims priority to Japanese Application No. 2018-116787, filed on Jun. 20, 2018, the entire disclosures of which are hereby incorporated by reference.

FIELD

The present invention relates to a blood purification apparatus for purifying a patient's blood while causing the blood to extracorporeally circulate in dialysis treatment or the like performed with a dialyzer, and also relates to a method of estimating a patient's state of nutrition on a blood purification apparatus.

BACKGROUND

In general, dialysis treatment is performed by using a blood circuit for causing blood collected from a patient to extracorporeally circulate and return into the body. Such a blood circuit basically includes, for example, an arterial blood circuit and a venous blood circuit that are connectable to a dialyzer (a blood purifier) including hollow fiber membranes. The arterial blood circuit and the venous blood circuit are provided at distal ends thereof with an arterial puncture needle and a venous puncture needle, respectively. The patient is punctured with the puncture needles, and extracorporeal circulation of blood in the dialysis treatment is thus performed.

In particular, the arterial blood circuit includes a squeezable tube and is provided with a peristaltic blood pump. The blood pump is capable of delivering liquid by squeezing the squeezable tube with rollers. When the blood pump is activated, the patient's blood can be caused to extracorporeally circulate through the blood circuit. Thus, the blood in extracorporeal circulation undergoes blood purification treatment in the dialyzer (see PTL 1, for example).

PTL 1: Japanese Unexamined Patent Application Publication No. 2013-27455 is incorporated by reference herein for all purposes.

SUMMARY

The above known blood purification apparatus has the following problem.

If the amount of protein, mainly albumin, contained in the patient's blood is insufficient, it can be said that the amount of protein taken in by the patient in everyday meals is insufficient. That is, the patient is presumed to be in a poor state of nutrition. The amount of protein, mainly albumin, can be grasped by, for example, detecting the plasma total protein of the patient's blood. Therefore, if some blood is collected in a medical examination and the plasma total protein is measured, the state of nutrition can be estimated.

Accordingly, the present applicant has decided to examine a blood purification apparatus in which the colloid osmotic pressure is calculated during the blood purification treatment by using blood purification membranes provided in a blood purifier so that parameters, such as plasma total protein, indicating the patient's state of nutrition can be grasped with reference to the calculated colloid osmotic pressure. Specifically, the present applicant has considered as follows. The blood purification membranes provided in the blood purifier do not allow substances such as protein, mainly albumin, to pass therethrough but allow substances smaller than those to pass therethrough. Hence, if the transmembrane pressure difference (the pressure difference between the blood flow route and the dialysate flow route, abbreviated to TMP) is detected by using the blood purification membranes, the colloid osmotic pressure of the patient's blood can be calculated.

Typically, however, a sensor that detects pressure involves error factors such as the difference between the high side and the low side (the head difference). Therefore, to correct such errors, the transmembrane pressure difference (TMP) occurring on the blood purification membranes of the blood purifier needs to be detected with the filtration by the ultrafiltration pump withheld, and the value detected in such a state needs to be used as a zero-adjusted value (for example, the transmembrane pressure difference is calculated by subtracting the zero-adjusted value from the actual detected value). In such a case, the zero adjustment is done for various error factors including colloid osmotic pressure. Therefore, the colloid osmotic pressure cannot be calculated.

The present invention has been conceived in view of the above circumstances and provides a blood purification apparatus capable of accurately calculating the colloid osmotic pressure or a correlation value of colloid osmotic pressure by utilizing blood purification membranes provided in a blood purifier, enabling accurate estimation of a patient's state of nutrition, and also provides a method of estimating a patient's state of nutrition on a blood purification apparatus.

Variation 1 may comprise a blood purification apparatus that includes a blood circuit including an arterial blood circuit and a venous blood circuit and that allows a patient's blood to extracorporeally circulate from a distal end of the arterial blood circuit to a distal end of the venous blood circuit; a blood purifier provided between the arterial blood circuit and the venous blood circuit and that purifies the blood flowing through the blood circuit, the blood purifier having a blood flow route through which the blood extracorporeally circulating through the blood circuit flows and a dialysate flow route through which dialysate flows, the blood flow route and the dialysate flow route being separated from each other by a blood purification membrane for purifying the blood; an ultrafiltration unit that performs ultrafiltration by filtering out water from the blood in the blood flow route through the blood purification membrane and draining the water through the dialysate flow route; and a detecting unit that detects a transmembrane pressure difference occurring on the blood purification membrane under a pressure difference between liquid in the blood flow route and liquid in the dialysate flow route. The blood purification apparatus includes a colloid-osmotic-pressure-acquiring unit that acquires a colloid osmotic pressure of the blood in the blood flow route or a correlation value of colloid osmotic pressure with reference to the transmembrane pressure difference occurring when liquid that does not generate colloid osmotic pressure is supplied into the blood flow route with the filtration by the ultrafiltration unit withheld and the transmembrane pressure difference occurring when the patient's blood is supplied into the blood flow route with the filtration by the ultrafiltration unit withheld.

Variation 2 may comprise the blood purification apparatus according to variation 1 and further includes a control unit that executes a first step in which the liquid that does not generate colloid osmotic pressure is supplied into the blood flow route with the filtration by the ultrafiltration unit withheld, and the transmembrane pressure difference is calculated by using the detecting unit; and a second step in which the patient's blood is supplied into the blood flow route with the filtration by the ultrafiltration unit withheld, and the transmembrane pressure difference is calculated by using the detecting unit. Furthermore, the colloid-osmotic-pressure-acquiring unit acquires the colloid osmotic pressure or the correlation value of colloid osmotic pressure with reference to the transmembrane pressure difference calculated in the first step and the transmembrane pressure difference calculated in the second step.

Variation 3 may comprise the blood purification apparatus according to variation 2 where the control unit is capable of sequentially executing a priming step in which a priming solution is supplied into the blood circuit and a treatment step in which blood purification treatment is performed with the blood purifier while the patient's blood is caused to extracorporeally circulate through the blood circuit. Furthermore, the liquid that does not generate colloid osmotic pressure and is supplied into the blood flow route in the first step is the priming solution that is used in the priming step, and the blood that is supplied into the blood flow route in the second step is the blood that is caused to extracorporeally circulate in the treatment step.

Variation 4 may comprise the blood purification apparatus according to variation 2 or 3 and wherein the control unit executes the first step and the second step while a flow of the liquid is stopped in the blood flow route and in the dialysate flow route.

Variation 5 may comprise the blood purification apparatus according to variations 1 to 4, wherein the detecting unit includes a blood-flow-route-side inlet-pressure-detecting unit that detects a blood pressure on an inlet side with respect to the blood flow route of the blood purifier; a blood-flow-route-side outlet-pressure-detecting unit that detects a blood pressure on an outlet side with respect to the blood flow route; a dialysate-flow-route-side inlet-pressure-detecting unit that detects a dialysate pressure on an inlet side with respect to the dialysate flow route of the blood purifier; and a dialysate-flow-route-side outlet-pressure-detecting unit that detects a dialysate pressure on an outlet side with respect to the dialysate flow route.

Variation 6 may comprise the blood purification apparatus according to variation 1, wherein the detecting unit is provided at a predetermined position. Furthermore, the transmembrane pressure difference occurring when the liquid that does not generate colloid osmotic pressure is supplied into the blood flow route with the filtration by the ultrafiltration unit withheld is storable as a theoretical value. Furthermore, the colloid-osmotic-pressure-acquiring unit acquires the colloid osmotic pressure of the blood in the blood flow route or the correlation value of colloid osmotic pressure with reference to the theoretical value and the transmembrane pressure difference occurring when the patient's blood is supplied into the blood flow route with the filtration by the ultrafiltration unit withheld.

Variation 7 may comprise the blood purification apparatus according to variations 1 to 6 further includes a plasma-total-protein-acquiring unit that acquires a plasma total protein or a correlation value of plasma total protein with reference to the colloid osmotic pressure or the correlation value of colloid osmotic pressure acquired by the colloid-osmotic-pressure-acquiring unit.

Variation 8 may comprise a method of estimating a patient's state of nutrition on a blood purification apparatus that includes a blood circuit including an arterial blood circuit and a venous blood circuit and that allows a patient's blood to extracorporeally circulate from a distal end of the arterial blood circuit to a distal end of the venous blood circuit; a blood purifier provided between the arterial blood circuit and the venous blood circuit and that purifies the blood flowing through the blood circuit, the blood purifier having a blood flow route through which the blood extracorporeally circulating through the blood circuit flows and a dialysate flow route through which dialysate flows, the blood flow route and the dialysate flow route being separated from each other by a blood purification membrane for purifying the blood; an ultrafiltration unit that performs ultrafiltration by filtering out water from the blood in the blood flow route through the blood purification membrane and draining the water through the dialysate flow route; and a detecting unit that detects a transmembrane pressure difference occurring on the blood purification membrane under a pressure difference between liquid in the blood flow route and liquid in the dialysate flow route. In the method, a colloid osmotic pressure of the blood in the blood flow route or a correlation value of colloid osmotic pressure is acquired with reference to the transmembrane pressure difference occurring when liquid that does not generate colloid osmotic pressure is supplied into the blood flow route with the filtration by the ultrafiltration unit withheld and the transmembrane pressure difference occurring when the patient's blood is supplied into the blood flow route with the filtration by the ultrafiltration unit withheld.

Variation 9 may comprise the method of estimating a patient's state of nutrition on a blood purification apparatus according to variation 8, wherein the apparatus further includes a control unit that executes a first step in which the liquid that does not generate colloid osmotic pressure is supplied into the blood flow route with the filtration by the ultrafiltration unit withheld, and the transmembrane pressure difference is calculated by using the detecting unit; and a second step in which the patient's blood is supplied into the blood flow route with the filtration by the ultrafiltration unit withheld, and the transmembrane pressure difference is calculated by using the detecting unit. Furthermore, the colloid osmotic pressure or the correlation value of colloid osmotic pressure is acquired with reference to the transmembrane pressure difference calculated in the first step and the transmembrane pressure difference calculated in the second step.

Variation 10 may comprise the method of estimating a patient's state of nutrition on a blood purification apparatus according to variation 9, wherein the control unit is capable of sequentially executing a priming step in which a priming solution is supplied into the blood circuit and a treatment step in which blood purification treatment is performed with the blood purifier while the patient's blood is caused to extracorporeally circulate through the blood circuit. Furthermore, the liquid that does not generate colloid osmotic pressure and is supplied into the blood flow route in the first step is the priming solution that is used in the priming step, and the blood that is supplied into the blood flow route in the second step is the blood that is caused to extracorporeally circulate in the treatment step.

Variation 11 may comprise the method of estimating a patient's state of nutrition on a blood purification apparatus according to variation 9 or 10, wherein the control unit executes the first step and the second step while a flow of the liquid is stopped in the blood flow route and in the dialysate flow route.

Variation 12 may comprise the method of estimating a patient's state of nutrition on a blood purification apparatus according to any of variations 8 to 11, wherein the detecting unit includes a blood-flow-route-side inlet-pressure-detecting unit that detects a blood pressure on an inlet side with respect to the blood flow route of the blood purifier; a blood-flow-route-side outlet-pressure-detecting unit that detects a blood pressure on an outlet side with respect to the blood flow route; a dialysate-flow-route-side inlet-pressure-detecting unit that detects a dialysate pressure on an inlet side with respect to the dialysate flow route of the blood purifier; and a dialysate-flow-route-side outlet-pressure-detecting unit that detects a dialysate pressure on an outlet side with respect to the dialysate flow route.

Variation 13 may comprise the method of estimating a patient's state of nutrition on a blood purification apparatus according to variation 8, wherein the detecting unit is provided at a predetermined position. Furthermore, the transmembrane pressure difference occurring when the liquid that does not generate colloid osmotic pressure is supplied into the blood flow route with the filtration by the ultrafiltration unit withheld is stored as a theoretical value. Furthermore, the colloid osmotic pressure of the blood in the blood flow route or the correlation value of colloid osmotic pressure is acquired with reference to the theoretical value and the transmembrane pressure difference occurring when the patient's blood is supplied into the blood flow route with the filtration by the ultrafiltration unit withheld.

Variation 14 may comprise the method of estimating a patient's state of nutrition on a blood purification apparatus according to any of variations 8 to 13, a plasma total protein or a correlation value of plasma total protein is acquired with reference to the acquired colloid osmotic pressure or the acquired correlation value of colloid osmotic pressure.

Variations 1 and 8 may comprise the colloid osmotic pressure of the blood in the blood flow route or the correlation value of colloid osmotic pressure is acquired with reference to the transmembrane pressure difference occurring when the liquid that does not generate colloid osmotic pressure is supplied into the blood flow route with the filtration by the ultrafiltration unit withheld and the transmembrane pressure difference occurring when the patient's blood is supplied into the blood flow route with the filtration by the ultrafiltration unit withheld. Therefore, the colloid osmotic pressure or the correlation value of colloid osmotic pressure can be calculated accurately by utilizing the blood purification membrane provided in the blood purifier. Consequently, the patient's state of nutrition can be estimated accurately.

Variations 2 and 9 may comprise the colloid osmotic pressure or the correlation value of colloid osmotic pressure is acquired with reference to the transmembrane pressure difference calculated in the first step and the transmembrane pressure difference calculated in the second step. Therefore, the colloid osmotic pressure or the correlation value of colloid osmotic pressure can be calculated more smoothly by utilizing the blood purification membrane provided in the blood purifier.

Variations 3 and 10 may comprise the liquid that does not generate colloid osmotic pressure and is supplied into the blood flow route in the first step is the priming solution that is used in the priming step, and the blood that is supplied into the blood flow route in the second step is the blood that is caused to extracorporeally circulate in the treatment step. Therefore, the colloid osmotic pressure or the correlation value of colloid osmotic pressure can be calculated accurately by efficiently utilizing the priming solution that is used in the priming step.

Variations 4 and 11 may comprise the first step and the second step are executed while the flow of the liquid is stopped in the blood flow route and in the dialysate flow route. Therefore, error factors (such as pressure loss) occurring with the flow of the liquid can be suppressed. Consequently, the colloid osmotic pressure or the correlation value of colloid osmotic pressure can be calculated more accurately.

Variations 5 and 12 may comprise the detecting unit includes the blood-flow-route-side inlet-pressure-detecting unit that detects the blood pressure on the inlet side with respect to the blood flow route of the blood purifier, the blood-flow-route-side outlet-pressure-detecting unit that detects the blood pressure on the outlet side with respect to the blood flow route, the dialysate-flow-route-side inlet-pressure-detecting unit that detects the dialysate pressure on the inlet side with respect to the dialysate flow route of the blood purifier, and the dialysate-flow-route-side outlet-pressure-detecting unit that detects the dialysate pressure on the outlet side with respect to the dialysate flow route. Therefore, the transmembrane pressure difference for calculating the colloid osmotic pressure or the correlation value of colloid osmotic pressure can be detected accurately and easily by efficiently utilizing the detecting units intended for a typical blood purification apparatus.

Variations 6 and 13 may comprise the detecting unit is provided at the predetermined position. Furthermore, the transmembrane pressure difference occurring when the liquid that does not generate colloid osmotic pressure is supplied into the blood flow route with the filtration by the ultrafiltration unit withheld is stored as a theoretical value. Furthermore, the colloid osmotic pressure of the blood in the blood flow route or the correlation value of colloid osmotic pressure is acquired with reference to the above theoretical value and the transmembrane pressure difference occurring when the patient's blood is supplied into the blood flow route with the filtration by the ultrafiltration unit withheld. Therefore, the colloid osmotic pressure or the correlation value of colloid osmotic pressure can be calculated more easily.

Variations 7 and 14 may comprise the plasma total protein or the correlation value of plasma total protein is acquired with reference to the acquired colloid osmotic pressure or the acquired correlation value of colloid osmotic pressure. Therefore, not only the colloid osmotic pressure or the correlation value of colloid osmotic pressure but also the plasma total protein or the correlation value of plasma total protein can be acquired as indices indicating the patient's state of nutrition. Consequently, the patient's state of nutrition can be grasped more accurately.

BRIEF DESCRIPTION OF THE DRAWINGS

FIG. 1 is a schematic diagram of a dialysis apparatus (a blood purification apparatus) according to a first embodiment of the present invention.

FIG. 2 is a flow chart of a control process executed by the dialysis apparatus.

FIG. 3 is a schematic diagram of the dialysis apparatus in a state established for a priming step.

FIG. 4 is a schematic diagram of the dialysis apparatus in a state established for a first step.

FIG. 5 is a schematic diagram of the dialysis apparatus in a state established for a treatment step.

FIG. 6 is a schematic diagram of the dialysis apparatus in a state established for a second step.

FIG. 7 is a schematic diagram of the dialysis apparatus in a state established for a modified second step.

FIG. 8 is a flow chart of a control process executed by a dialysis apparatus (a blood purification apparatus) according to a second embodiment of the present invention.

FIG. 9 is a schematic diagram of a dialysis apparatus (a blood purification apparatus) according to another embodiment of the present invention.

DETAILED DESCRIPTION

Embodiments of the present invention will now be described specifically with reference to the drawings.

A blood purification apparatus according to a first embodiment is a dialysis apparatus for giving dialysis treatment and includes, as illustrated in FIG. 1, a blood circuit including an arterial blood circuit 1 and a venous blood circuit 2, a dialyzer 3 (a blood purifier) that purifies blood flowing through the blood circuit, an arterial air-trap chamber 5 connected to the arterial blood circuit 1, a venous air-trap chamber 6 connected to the venous blood circuit 2, a duplex pump 7, an ultrafiltration pump 8 (an ultrafiltration unit), a control unit 10, a colloid-osmotic-pressure-acquiring unit 11, a plasma-total-protein-acquiring unit 12, a display 13, and a storage unit 14.

The arterial blood circuit 1 is provided with an arterial puncture needle (a) connected to a distal end thereof through a connector (c). A peristaltic blood pump 4 and the arterial air-trap chamber 5 are provided at respective halfway positions of the arterial blood circuit 1. The venous blood circuit 2 is provided with a venous puncture needle (b) connected to a distal end thereof through a connector (d). The venous air-trap chamber 6 is connected to a halfway position of the venous blood circuit 2. Furthermore, a distal portion (near the connector (c)) of the arterial blood circuit 1 and a distal portion (near the connector (d)) of the venous blood circuit 2 are provided with an electromagnetic valve V1 and an electromagnetic valve V2, respectively, which are capable of arbitrarily closing or opening respective flow routes.

In the dialysis treatment, when the blood pump 4 is activated while a patient is punctured with the arterial puncture needle (a) and the venous puncture needle (b), the patient's blood flows through the arterial blood circuit 1 and reaches the dialyzer 3, where the blood is purified. Then, the blood flows through the venous blood circuit 2 and returns into the patient's body. That is, the dialysis treatment (blood purification treatment) is performed by purifying the patient's blood with the dialyzer 3 while causing the blood to extracorporeally circulate through the blood circuit from the distal end of the arterial blood circuit 1 to the distal end of the venous blood circuit 2. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The arterial air-trap chamber 5 is provided with an overflow line La. The overflow line La extends from the top of the arterial air-trap chamber 5, with a distal end thereof open to the atmosphere. The overflow line La allows liquid (a priming solution) overflowing from the arterial air-trap chamber 5 to be discharged to the outside. The overflow line La is provided with an electromagnetic valve V3, which is capable of closing or opening a flow route as the overflow line La at an arbitrary timing.

The dialyzer 3 has, in a housing thereof, a blood inlet 3a (a blood introduction port), a blood outlet 3b (a blood delivery port), a dialysate inlet 3c (a dialysate introduction port), and a dialysate outlet 3d (a dialysate delivery port). The blood inlet 3a is connected to a proximal end of the arterial blood circuit 1. The blood outlet 3b is connected to a proximal end of the venous blood circuit 2. The dialysate inlet 3c and the dialysate outlet 3d are connected to a dialysate introduction line L1 and a dialysate drain line L2, respectively, extending from a dialysis device.

The dialyzer 3 houses a plurality of hollow fibers 3e. The hollow fibers 3e form blood purification membranes for purifying blood. The dialyzer 3 has blood flow routes (each extending between the blood inlet 3a and the blood outlet 3b) through which the patient's blood flows and dialysate flow routes (each extending between the dialysate inlet 3c and the dialysate outlet 3d) through which dialysate flows. The blood flow routes and the dialysate flow routes are separated from each other by the hollow fibers 3e (blood purification membranes). The hollow fibers 3e forming blood purification membranes each have a number of microscopic holes (pores) extending therethrough from the outer surface to the inner surface, thereby forming a hollow fiber membrane. Impurities and the like contained in the blood are allowed to permeate through the membranes into the dialysate.

The duplex pump 7 is provided over the dialysate introduction line L1 and the dialysate drain line L2 in the dialysis device. The dialysate drain line L2 is provided with a bypass line L3 that bypasses the duplex pump 7. The bypass line L3 is provided with the ultrafiltration pump 8 (the ultrafiltration unit) for removing water from the patient's blood flowing through the blood flow routes in the dialyzer 3. With the activation of the ultrafiltration pump 8, the pressure in the dialysate flow routes can be made lower than (negative to) the pressure in the blood flow routes in the dialyzer 3. Therefore, water is filtered out from the blood in the blood flow routes through the hollow fibers 3e (the blood purification membranes) and is drained through the dialysate flow routes, whereby ultrafiltration is achieved. The dialysate drain line L2 is further provided with a bypass line L4 that bypasses the duplex pump 7 and the ultrafiltration pump 8. The bypass line L4 is provided with an electromagnetic valve V6, which is capable of closing or opening a flow route as the bypass line L4 at an arbitrary timing.

The dialysate introduction line L1 forms a flow route for introducing the dialysate into the dialyzer 3. One end of the dialysate introduction line L1 is connected to the dialysate inlet 3c of the dialyzer 3, and the other end is connected to a dialysate supply device (not illustrated) that prepares a dialysate at a predetermined concentration. The dialysate drain line L2 forms a flow route for delivering waste liquid drained from the dialyzer 3. One end of the dialysate drain line L2 is connected to the dialysate outlet 3d of the dialyzer 3, and the other end is connected to a drainage unit, not illustrated.

Hence, when the duplex pump 7 is activated, the dialysate supplied from the dialysate supply device flows through the dialysate introduction line L1 into the dialyzer 3, and further flows through the dialysate drain line L2 into the drainage unit. The dialysate introduction line L1 and the dialysate drain line L2 are provided with an electromagnetic valve V4 and an electromagnetic valve V5 near respective points of connection to the dialyzer 3. Therefore, the flow routes as the dialysate introduction line L1 and the dialysate drain line L2 are each closable or openable at an arbitrary timing.

A priming-solution supply line Lb is connected at one end thereof to a connecting portion 9 defined at a predetermined position of the dialysate introduction line L1 between the duplex pump 7 and the dialyzer 3. The other end of the priming-solution supply line Lb is connected to a predetermined position of the arterial blood circuit 1 between the blood pump 4 and the electromagnetic valve V1. The priming-solution supply line Lb is provided with an electromagnetic valve V7 capable of closing or opening the flow route thereof at an arbitrary timing. When the electromagnetic valve V7 is opened, the dialysate (the priming solution) in the dialysate introduction line L1 can be supplied into the arterial blood circuit 1.

According to the present embodiment, detecting units (a blood-flow-route-side inlet-pressure-detecting unit P1, a blood-flow-route-side outlet-pressure-detecting unit P2, a dialysate-flow-route-side inlet-pressure-detecting unit P3, and a dialysate-flow-rate-side outlet-pressure-detecting unit P4) that are capable of detecting the transmembrane pressure difference occurring on the hollow fibers 3e (the blood purification membranes) under a pressure difference between the liquid in the blood flow routes and the liquid in the dialysate flow routes are provided near respective points of connection between the dialyzer 3 and the proximal end of the arterial blood circuit 1, the proximal end of the venous blood circuit 2, the one end of the dialysate introduction line L1, and the one end of the dialysate drain line L2.

That is, the detecting units include the blood-flow-route-side inlet-pressure-detecting unit P1 that detects the blood pressure on the inlet side with respect to the blood flow routes of the dialyzer 3, the blood-flow-route-side outlet-pressure-detecting unit P2 that detects the blood pressure on the outlet side with respect to the blood flow routes, the dialysate-flow-route-side inlet-pressure-detecting unit P3 that detects the dialysate pressure on the inlet side with respect to the dialysate flow routes of the dialyzer 3, and the dialysate-flow-route-side outlet-pressure-detecting unit P4 that detects the dialysate pressure on the outlet side with respect to the dialysate flow routes.

Letting the value detected by the blood-flow-route-side inlet-pressure-detecting unit P1 be PBi, the value detected by the blood-flow-route-side outlet-pressure-detecting unit P2 be PBo, the value detected by the dialysate-flow-route-side inlet-pressure-detecting unit P3 be PDi, and the value detected by the dialysate-flow-route-side outlet-pressure-detecting unit P4 be PDo, the transmembrane pressure difference (TMP) occurring on the hollow fibers 3e (the blood purification membranes) can be calculated through Math. given below.

$$TMP = (PBi + PBo)/2 - (PDi + PDo)/2 \quad \text{Math.}$$

The control unit 10 is a microcomputer or the like provided in the dialysis device and controls the opening/closing of the electromagnetic valves V1 to V7 and the driving of the actuators (such as the blood pump 4, the duplex pump 7, and the ultrafiltration pump 8). The control unit 10 according to the present embodiment is capable of sequentially executing a priming step (see FIG. 3) in which the priming solution (in the present embodiment, the dialysate supplied through the priming-solution supply line Lb) is supplied into the blood circuit, a treatment step (see FIG. 5) in which dialysis treatment (blood purification treatment) is performed with the dialyzer 3 while the patient's blood is caused to extracorporeally circulate through the blood circuit, and a blood-return step in which the blood in the blood circuit is returned to the patient after the dialysis treatment.

The control unit 10 according to the present embodiment is capable of executing a first step (see FIG. 4) in which liquid that does not generate colloid osmotic pressure is supplied into the blood flow routes with the filtration by the ultrafiltration pump 8 (the ultrafiltration unit) withheld (with the ultrafiltration pump 8 stopped), and the transmembrane pressure difference (TMPa) is calculated by using the detecting units (P1 to P4); and a second step (see FIG. 6) in which the patient's blood is supplied into the blood flow routes with the filtration by the ultrafiltration pump 8 (the ultrafiltration unit) withheld (with the ultrafiltration pump 8 stopped), and the transmembrane pressure difference (TMPb) is calculated by using the detecting units (P1 to P4).

In the present embodiment, the liquid that does not generate colloid osmotic pressure and is supplied into the blood flow routes in the first step is the priming solution that is used in the priming step (in the present embodiment, the dialysate that is supplied through the priming-solution supply line Lb), and the blood that is supplied into the blood flow routes in the second step is the blood that is caused to extracorporeally circulate in the treatment step. Before the treatment step, a gas-purging step for supplying the dialysate into the dialysate flow routes in the dialyzer 3 is executed.

The colloid-osmotic-pressure-acquiring unit 11 acquires the colloid osmotic pressure (CP) of the blood in the blood flow routes with reference to the transmembrane pressure difference (TMPa) occurring when the liquid (the priming solution) that does not generate colloid osmotic pressure is supplied into the blood flow routes with the filtration by the ultrafiltration pump 8 withheld and the transmembrane pressure difference (TMPb) occurring when the patient's blood is supplied into the blood flow routes with the filtration by the ultrafiltration pump 8 withheld. In the present embodiment, the colloid-osmotic-pressure-acquiring unit 11 is capable of acquiring the colloid osmotic pressure (CP) by calculating the difference between TMPa and TMPb (TMPb−TMPa).

In the present embodiment, the colloid osmotic pressure is acquired by calculating the difference between TMPa and TMPb. Alternatively, the colloid osmotic pressure (CP) may be acquired with reference to, for example, a table summarizing the relationship between colloid osmotic pressure (CP) and each of TMPa and TMPb. Moreover, the colloid-osmotic-pressure-acquiring unit 11 is not limited to the one that acquires the colloid osmotic pressure (CP) and may be the one that acquires a correlation value of colloid osmotic pressure (such as the ratio between TMPa and TMPb, or a value obtained by multiplying the colloid osmotic pressure (CP) by a predetermined coefficient) through calculation, with reference to a table, or by any other like means.

The plasma-total-protein-acquiring unit 12 acquires the plasma total protein (TP), which tells the amount (g/dL) of proteins such as albumin contained in the blood, with reference to the colloid osmotic pressure or the correlation value of colloid osmotic pressure acquired by the colloid-osmotic-pressure-acquiring unit 11. In the present embodiment, TP is solved from the following relational expression.

$$CP \text{ (colloid osmotic pressure)} = 2.1(TP) + 0.16(TP)^2 + 0.009(TP)^3$$

In the present embodiment, the plasma total protein is acquired by calculating TP through the above relational expression. Alternatively, the plasma total protein (TP) may be acquired with reference to, for example, a table summarizing the relationship between plasma total protein (TP) and colloid osmotic pressure (CP). Moreover, the plasma-total-protein-acquiring unit 12 is not limited to the one that acquires the plasma total protein (TP) and may be the one that acquires a correlation value of plasma total protein (such as a value obtained by multiplying the plasma total protein (TP) by a predetermined coefficient) through calculation, with reference to a table, or by any other like means.

The display 13 is a screen such as a liquid-crystal monitor and is capable of displaying the colloid osmotic pressure or the correlation value of colloid osmotic pressure acquired by the colloid-osmotic-pressure-acquiring unit 11. The display 13 according to the present embodiment is capable of displaying not only the colloid osmotic pressure or the correlation value of colloid osmotic pressure but also the plasma total protein or the correlation value of plasma total protein acquired by the plasma-total-protein-acquiring unit 12. With reference to the colloid osmotic pressure or the correlation value of colloid osmotic pressure and the plasma total protein or the correlation value of plasma total protein displayed on the display 13, medical workers including doctors can estimate the patient's state of nutrition.

The storage unit 14 is a storage medium and is capable of storing the colloid osmotic pressure or the correlation value of colloid osmotic pressure acquired by the colloid-osmotic-pressure-acquiring unit 11, and the plasma total protein or the correlation value of plasma total protein acquired by the plasma-total-protein-acquiring unit 12. The colloid osmotic pressure or the correlation value of colloid osmotic pressure, or the plasma total protein or the correlation value of plasma total protein stored in the storage unit 14 is preferred to be linked to other pieces of patient information and may be transmitted to a server or the like capable of transmitting and receiving information to and from the dialysis apparatus.

Now, a control process executed by the control unit 10 according to the present embodiment will be described with reference to a flow chart illustrated in FIG. 2.

First, before the treatment, the priming step and the gas-purging step are executed (S1). This step, S1, is executed as follows. As illustrated in FIG. 3, the connector (c) and the connector (d) are connected to each other to make the respective flow routes communicate with each other. Then, with the electromagnetic valves V4 and V5 closed, the electromagnetic valves V1 to V3, V6, and V7 are opened. Furthermore, the blood pump 4 and the duplex pump 7 are activated, with the ultrafiltration pump 8 stopped.

Accordingly, the dialysate (the priming solution) in the dialysate introduction line L1 flows through the priming-solution supply line Lb into the blood circuit and fills the blood circuit. Then, the dialysate (the priming solution) is discharged to the outside through the overflow line La. Thus, the priming step is achieved. Subsequently, with the electromagnetic valves V6 and V7 closed, the electromagnetic valves V4 and V5 are opened. Accordingly, the dialysate flows into the dialysate flow routes in the dialyzer 3. Thus, the gas-purging step is achieved.

Subsequently, the first step, S2, is executed in which liquid that does not generate colloid osmotic pressure (the priming solution used in the priming step in S1) is supplied into the blood flow routes with the filtration (ultrafiltration) by the ultrafiltration pump 8 (the ultrafiltration unit) withheld, and the transmembrane pressure difference (TMPa) is calculated by using the detecting units (P1 to P4). Specifically, the first step S2 is executed as follows. As illustrated in FIG. 4, with the electromagnetic valves V3, V6, and V7 closed, the electromagnetic valves V1, V2, V4, and V5 are opened. Furthermore, with the blood pump 4 and the duplex pump 7 kept activated and the ultrafiltration pump 8 kept stopped, the transmembrane pressure difference (TMPa) is calculated from the values detected by the detecting units (P1 to P4).

Subsequently, the treatment step, S3, is executed in which blood purification treatment is performed with the dialyzer 3 while the patient's blood is caused to extracorporeally circulate through the blood circuit. The treatment step S3 is executed as follows. As illustrated in FIG. 5, the connector (c) and the connector (d) are disconnected from each other, and the arterial puncture needle (a) and the venous puncture needle (b) are connected thereto, respectively. Then, with the electromagnetic valves V3, V6, and V7 closed, the electromagnetic valves V1, V2, V4, and V5 are opened. Furthermore, the blood pump 4, the duplex pump 7, and the ultrafiltration pump 8 are activated.

Thus, the patient's blood is substituted for the priming solution (the dialysate) in the blood circuit and extracorporeally circulates therethrough. In the process of extracorporeal circulation, blood purification treatment is achieved with the dialyzer 3. Furthermore, since the ultrafiltration pump 8 is activated, water can be filtered out from the blood in the blood flow routes through the hollow fibers 3e (the blood purification membranes) and be drained through the dialysate flow routes. Thus, ultrafiltration is achieved.

Subsequently, in S4, whether or not a predetermined time has elapsed since the start of the treatment is checked. If it is determined that the predetermined time has elapsed, the ultrafiltration pump 8 is stopped to stop the filtration (ultrafiltration) (S5). Then, the second step, S6, is executed in which the patient's blood is supplied into the blood flow routes with the filtration (ultrafiltration) by the ultrafiltration pump 8 (the ultrafiltration unit) withheld, and the transmembrane pressure difference (TMPb) is calculated by using the detecting units (P1 to P4). Specifically, the second step S6 is executed as follows. As illustrated in FIG. 6, with the electromagnetic valves V3, V6, and V7 closed, the electromagnetic valves V1, V2, V4, and V5 are opened. Furthermore, with the blood pump 4 and the duplex pump 7 kept activated and the ultrafiltration pump 8 stopped, the transmembrane pressure difference (TMPb) is calculated from the values detected by the detecting units (P1 to P4).

Subsequently, the colloid osmotic pressure (CP) or the correlation value of colloid osmotic pressure (CP) is acquired from TMPa and TMPb through calculation by the colloid-osmotic-pressure-acquiring unit 11 (S7). Furthermore, the plasma total protein (TP) or the correlation value of plasma total protein (TP) is acquired with reference to the colloid osmotic pressure (CP) or the correlation value of colloid osmotic pressure (CP) acquired as above, through calculation by the plasma-total-protein-acquiring unit 12 (S8). The colloid osmotic pressure (CP) or the correlation value of colloid osmotic pressure (CP) and the plasma total protein (TP) or the correlation value of plasma total protein (TP) acquired as above are displayed on the display 13 and stored in the storage unit 14 (S9).

As described above, in the present embodiment, the control unit 10 is employed that executes the first step S2 in which liquid that does not generate colloid osmotic pressure (the dialysate as the priming solution) is supplied into the blood flow routes with the filtration by the ultrafiltration pump 8 (the ultrafiltration unit) withheld, and the transmembrane pressure difference (TMPa) is calculated by using the detecting units (P1 to P4); and the second step S6 in which the patient's blood is supplied into the blood flow routes with the filtration by the ultrafiltration pump 8 (the ultrafiltration unit) withheld, and the transmembrane pressure difference (TMPb) is calculated by using the detecting units (P1 to P4). Furthermore, the colloid-osmotic-pressure-acquiring unit 11 is capable of acquiring the colloid osmotic pressure or the correlation value of colloid osmotic pressure with reference to the transmembrane pressure difference (TMPa) calculated in the first step S2 and the transmembrane pressure difference (TMPb) calculated in the second step S6.

Note that as long as the colloid osmotic pressure (CP) or the correlation value of colloid osmotic pressure (CP) is displayed and stored in S9, the plasma total protein (TP) or the correlation value of plasma total protein (TP) does not necessarily need to be acquired (if so, neither the plasma total protein (TP) nor the correlation value of plasma total protein (TP) is displayed and stored). Alternatively, for example, the colloid osmotic pressure (CP) or the correlation value of colloid osmotic pressure (CP) and the plasma total protein (TP) or the correlation value of plasma total protein (TP) may be displayed without being stored, or may be stored without being displayed. As another alternative, the colloid osmotic pressure (CP) or the correlation value of colloid osmotic pressure (CP) and the plasma total protein (TP) or the correlation value of plasma total protein (TP) may be transmitted to an external server or the like without being displayed nor stored.

In each of the first step S2 and the second step S6, the control unit 10 according to the present embodiment operates such that the transmembrane pressure difference (TMPa or TMPb) is calculated with the blood pump 4 and the duplex pump 7 activated. Alternatively, the transmembrane pressure difference (TMPa or TMPb) may be calculated with the blood pump 4 and the duplex pump 7 stopped. In the latter case, the second step S6, for example, is executed in the following state (the same applies to the first step S2). As illustrated in FIG. 7, the electromagnetic valves V3, V6, and V7 are closed; the electromagnetic valves V1, V2, V4, and V5 are opened; and the blood pump 4, the duplex pump 7, and the ultrafiltration pump 8 are stopped.

In the above control process, the first step S2 and the second step S6 can be executed while the flow of the liquid is stopped in the blood flow routes and in the dialysate flow routes. Therefore, error factors, such as pressure loss due to the flow of the liquid in the blood flow routes and in the dialysate flow routes and the occurrence of filtration due to unbalanced driving of the duplex pump 7, can be suppressed. Consequently, the colloid osmotic pressure or the correlation value of colloid osmotic pressure (and the plasma total protein or the correlation value of plasma total protein) can be calculated more accurately.

Furthermore, since the flow of the liquid is stopped in the blood flow routes and in the dialysate flow routes, hydraulic pressures at a position of the arterial blood circuit 1 that is on the upstream (inlet) side with respect to the dialyzer 3, a position of the venous blood circuit 2 that is on the downstream (outlet) side with respect to the dialyzer 3, a position of the dialysate introduction line L1 that is on the upstream (inlet) side with respect to the dialyzer 3, and a position of the dialysate drain line L2 that is on the downstream (outlet) side with respect to the dialyzer 3 become substantially equal. Therefore, TMPa or TMPb can be calculated from one of the value detected by the blood-flow-route-side inlet-pressure-detecting unit P1 and the value detected by the blood-flow-route-side outlet-pressure-detecting unit P2, and one of the value detected by the dialysate-flow-route-side inlet-pressure-detecting unit P3 and the value detected by the dialysate-flow-route-side outlet-pressure-detecting unit P4.

According to the present embodiment, the colloid osmotic pressure of the blood in the blood flow routes or the correlation value of colloid osmotic pressure is acquired with reference to the transmembrane pressure difference (TMPa) occurring when the liquid that does not generate colloid osmotic pressure is supplied into the blood flow routes with the filtration by the ultrafiltration pump 8 (the ultrafiltration unit) withheld and the transmembrane pressure difference (TMPb) occurring when the patient's blood is supplied into the blood flow routes with the filtration by the ultrafiltration pump 8 (the ultrafiltration unit) withheld. Therefore, the colloid osmotic pressure or the correlation value of colloid osmotic pressure can be calculated accurately by utilizing the hollow fibers 3e (the blood purification membranes) provided in the dialyzer 3 (the blood purifier). Consequently, the patient's state of nutrition can be estimated accurately.

Furthermore, the colloid osmotic pressure or the correlation value of colloid osmotic pressure is acquired with reference to the transmembrane pressure difference (TMPa) calculated in the first step and the transmembrane pressure difference (TMPb) calculated in the second step. Therefore, the colloid osmotic pressure or the correlation value of colloid osmotic pressure can be calculated more smoothly by utilizing the hollow fibers 3e (the blood purification membranes) provided in the dialyzer 3 (the blood purifier). Furthermore, the liquid that does not generate colloid osmotic pressure and is supplied into the blood flow routes in the first step is the priming solution that is used in the priming step, and the blood that is supplied into the blood flow routes in the second step is the blood that is caused to extracorporeally circulate in the treatment step. Therefore, the colloid osmotic pressure or the correlation value of colloid osmotic pressure can be calculated accurately by efficiently utilizing the priming solution that is used in the priming step.

Furthermore, the detecting units according to the present embodiment include the blood-flow-route-side inlet-pressure-detecting unit P1 that detects the blood pressure on the inlet side with respect to the blood flow routes of the dialyzer 3 (the blood purifier), the blood-flow-route-side outlet-pressure-detecting unit P2 that detects the blood pressure on the outlet side with respect to the blood flow routes, the dialysate-flow-route-side inlet-pressure-detecting unit P3 that detects the dialysate pressure on the inlet side with respect to the dialysate flow routes of the dialyzer 3 (the blood purifier), and the dialysate-flow-route-side outlet-pressure-detecting unit P4 that detects the dialysate pressure on the outlet side with respect to the dialysate flow routes. Therefore, the transmembrane pressure difference for calculating the colloid osmotic pressure or the correlation value of colloid osmotic pressure can be detected accurately and easily by efficiently utilizing the detecting units intended for a typical blood purification apparatus.

Furthermore, according to the present embodiment, the plasma total protein or the correlation value of plasma total protein is acquired with reference to the acquired colloid osmotic pressure or the acquired correlation value of colloid osmotic pressure. Therefore, not only the colloid osmotic pressure or the correlation value of colloid osmotic pressure but also the plasma total protein or the correlation value of plasma total protein can be acquired as indices indicating the patient's state of nutrition. Consequently, the patient's state of nutrition can be grasped more accurately. Note that any other indices that can help estimate the patient's state of nutrition may be calculated with reference to the acquired colloid osmotic pressure or the acquired correlation value of colloid osmotic pressure.

Now, a second embodiment of the present invention will be described.

As with the case of the first embodiment, a blood purification apparatus according to the present embodiment is a dialysis apparatus for giving dialysis treatment and includes, as illustrated in FIG. 1, a blood circuit including an arterial blood circuit 1 and a venous blood circuit 2, a dialyzer 3 (a blood purifier) that purifies blood flowing through the blood circuit, an arterial air-trap chamber 5 connected to the arterial blood circuit 1, a venous air-trap chamber 6 connected to the venous blood circuit 2, a duplex pump 7, an ultrafiltration pump 8 (an ultrafiltration unit), a control unit 10, a colloid-osmotic-pressure-acquiring unit 11, a plasma-total-protein-acquiring unit 12, a display 13, and a storage unit 14. The configuration of the apparatus is the same as that described in the first embodiment, and detailed description thereof is omitted.

In the present embodiment, the blood circuit is fixed at a predetermined position, and the detecting units (P1 to P4) are provided at respective predetermined positions. The storage unit 14 is capable of storing, as a theoretical value, the transmembrane pressure difference (TMPa) occurring when the liquid that does not generate colloid osmotic pressure (the dialysate as the priming solution) is supplied into the blood flow routes with the filtration by the ultrafiltration pump 8 (the ultrafiltration unit) withheld. The colloid-osmotic-pressure-acquiring unit 11 is capable of acquiring the colloid osmotic pressure of the blood in the blood flow routes or the correlation value of colloid osmotic pressure with reference to the above theoretical value and the transmembrane pressure difference (TMPb) occurring when the patient's blood is supplied into the blood flow routes with the filtration by the ultrafiltration pump 8 (the ultrafiltration unit) withheld.

Now, a control process executed by the control unit 10 according to the present embodiment will be described with reference to a flow chart illustrated in FIG. 8.

First, the transmembrane pressure difference (TMPa) occurring when the liquid that does not generate colloid osmotic pressure is supplied into the blood flow routes with the filtration by the ultrafiltration pump 8 withheld is stored as a theoretical value in advance in the storage unit 14. Then, before the treatment, the priming step and the gas-purging step are executed (S1). This step, S1, is executed as follows. As illustrated in FIG. 3, the connector (c) and the connector (d) are connected to each other to make the respective flow routes communicate with each other. Then, with the electromagnetic valves V4 and V5 closed, the electromagnetic valves V1 to V3, V6, and V7 are opened. Furthermore, the blood pump 4 and the duplex pump 7 are activated, with the ultrafiltration pump 8 stopped.

Accordingly, the dialysate (the priming solution) in the dialysate introduction line L1 flows through the priming-solution supply line Lb into the blood circuit and fills the blood circuit. Then, the dialysate (the priming solution) is discharged to the outside through the overflow line La. Thus, the priming step is achieved. Subsequently, with the electromagnetic valves V6 and V7 closed, the electromagnetic valves V4 and V5 are opened. Accordingly, the dialysate flows into the dialysate flow routes in the dialyzer 3. Thus, the gas-purging step is achieved.

Subsequently, the treatment step, S2, is executed in which blood purification treatment is performed with the dialyzer 3 while the patient's blood is caused to extracorporeally circulate through the blood circuit. The treatment step S2 is executed as follows. As illustrated in FIG. 5, the connector (c) and the connector (d) are disconnected from each other, and the arterial puncture needle (a) and the venous puncture needle (b) are connected thereto, respectively. Then, with the electromagnetic valves V3, V6, and V7 closed, the electromagnetic valves V1, V2, V4, and V5 are opened. Furthermore, the blood pump 4, the duplex pump 7, and the ultrafiltration pump 8 are activated.

Thus, the patient's blood is substituted for the priming solution (the dialysate) in the blood circuit and extracorporeally circulates therethrough. In the process of extracorporeal circulation, blood purification treatment is achieved with the dialyzer 3. Furthermore, since the ultrafiltration pump 8 is activated, water can be filtered out from the blood in the blood flow routes through the hollow fibers 3e (the blood purification membranes) and be drained through the dialysate flow routes. Thus, ultrafiltration is achieved.

Subsequently, in S3, whether or not a predetermined time has elapsed since the start of the treatment is checked. If it is determined that the predetermined time has elapsed, the ultrafiltration pump 8 is stopped to stop the filtration (ultrafiltration) (S4). Then, the second step, S5, is executed in which the patient's blood is supplied into the blood flow routes with the filtration (ultrafiltration) by the ultrafiltration pump 8 (the ultrafiltration unit) withheld, and the transmembrane pressure difference (TMPb) is calculated by using the detecting units (P1 to P4). Specifically, the second step S5 is executed as follows. As illustrated in FIG. 6, with the electromagnetic valves V3, V6, and V7 closed, the electromagnetic valves V1, V2, V4, and V5 are opened. Furthermore, with the blood pump 4 and the duplex pump 7 kept activated and the ultrafiltration pump 8 stopped, the transmembrane pressure difference (TMPb) is calculated from the values detected by the detecting units (P1 to P4).

Subsequently, the colloid osmotic pressure (CP) or the correlation value of colloid osmotic pressure (CP) is acquired from TMPa, which is the prestored theoretical value, and TMPb, which is the actual measured value, through calculation by the colloid-osmotic-pressure-acquiring unit 11 (S6). Furthermore, the plasma total protein (TP) or the correlation value of plasma total protein (TP) is acquired with reference to the colloid osmotic pressure (CP) or the correlation value of colloid osmotic pressure (CP) acquired as above, through calculation by the plasma-total-protein-acquiring unit 12 (S7). The colloid osmotic pressure (CP) or the correlation value of colloid osmotic pressure (CP) and the plasma total protein (TP) or the correlation value of plasma total protein (TP) acquired as above are displayed on the display 13 and stored in the storage unit 14 (S8).

According to the present embodiment, the detecting units (P1 to P4) are provided at the respective predetermined positions. Furthermore, the transmembrane pressure difference (TMPa) occurring when the liquid that does not generate colloid osmotic pressure is supplied into the blood flow routes with the filtration by the ultrafiltration pump 8 (the ultrafiltration unit) withheld is stored as a theoretical value. Furthermore, the colloid osmotic pressure of the blood in the blood flow routes or the correlation value of colloid osmotic pressure is acquired with reference to the above theoretical value and the transmembrane pressure difference (TMPb) occurring when the patient's blood is supplied into the blood flow routes with the filtration by the ultrafiltration pump 8 (the ultrafiltration unit) withheld. Therefore, it is not necessary to acquire the transmembrane pressure difference (TMPa) as the actual measured value. Consequently, the colloid osmotic pressure or the correlation value of colloid osmotic pressure can be calculated more easily.

While some embodiments have been described above, the present invention is not limited thereto. For example, as illustrated in FIG. 9, the priming-solution supply line Lb may be replaced with a priming-solution supply line Lc connected to a bag D (a saline bag) storing physiological saline, so that the physiological saline can be supplied as the priming solution. In such a case, the liquid that does not generate colloid osmotic pressure is preferred to be the physiological saline as the priming solution. The liquid that does not generate colloid osmotic pressure may be another kind of liquid different from dialysate or physiological saline.

Furthermore, the acquisition of the colloid osmotic pressure or the correlation value of colloid osmotic pressure is not limited to be executed once in an early stage of the treatment. The second step may be executed plural times during the treatment, so that the colloid osmotic pressure or the correlation value of colloid osmotic pressure is acquired each of the plural times. While the above embodiments are each applied to a dialysis apparatus intended for dialysis treatment, the present invention may also be applied to an apparatus (such as a blood purification apparatus or a plasma adsorption apparatus intended for hemodiafiltration, hemofiltration, or AFBF) that is capable of purifying a patient's blood while causing the blood to extracorporeally circulate.

The present invention is applicable to any blood purification apparatus and any method of estimating a patient's state of nutrition on a blood purification apparatus that are in any other mode and for any other use, as long as the colloid osmotic pressure of blood in a blood flow route or the correlation value of colloid osmotic pressure is acquired with reference to the transmembrane pressure difference occurring when liquid that does not generate colloid osmotic pressure is supplied into the blood flow route with the filtration by an ultrafiltration unit withheld and the transmembrane pressure difference occurring when the patient's blood is supplied into the blood flow route with the filtration by the ultrafiltration unit withheld.

REFERENCE SIGNS LIST 1 arterial blood circuit
2 venous blood circuit
3 dialyzer (blood purifier)
3a blood inlet
3b blood outlet
3c dialysate inlet
3d dialysate outlet
3e hollow fiber (blood purification membrane)
4 blood pump
5 arterial air-trap chamber
6 venous air-trap chamber
7 duplex pump
8 ultrafiltration pump (ultrafiltration unit)
9 connecting portion
10 control unit
11 colloid-osmotic-pressure-acquiring unit
12 plasma-total-protein-acquiring unit
13 display
14 storage unit
P1 blood-flow-route-side inlet-pressure-detecting unit
P2 blood-flow-route-side outlet-pressure-detecting unit
P3 dialysate-flow-route-side inlet-pressure-detecting unit
P4 dialysate-flow-route-side outlet-pressure-detecting unit L1 dialysate introduction line
L2 dialysate drain line
L3 bypass line
L4 bypass line
La overflow line
Lb priming-solution supply line

The invention claimed is:

1. A blood purification apparatus that includes
a blood circuit including an arterial blood circuit and a venous blood circuit and that allows a patient's blood to extracorporeally circulate from a distal end of the arterial blood circuit to a distal end of the venous blood circuit;
a blood purifier provided between the arterial blood circuit and the venous blood circuit and that purifies the patient's blood flowing through the blood circuit, the blood purifier having a blood flow route through which the patient's blood extracorporeally circulating through the blood circuit flows and a dialysate flow route through which dialysate flows, the blood flow route and the dialysate flow route being separated from each other by a blood purification membrane for purifying the patient's blood;
an ultrafiltration unit that performs ultrafiltration by filtering out water from the patient's blood in the blood flow route through the blood purification membrane and draining the water through the dialysate flow route; and
a detecting unit that detects a transmembrane pressure difference occurring on the blood purification membrane under a pressure difference between liquid in the blood flow route and liquid in the dialysate flow route,
the blood purification apparatus comprising:
a blood pump;
a dialysate pump;
a colloid-osmotic-pressure-acquiring unit that acquires a colloid osmotic pressure of the patient's blood in the blood flow route or a correlation value of colloid osmotic pressure with reference to the transmembrane pressure difference occurring when liquid that does not generate colloid osmotic pressure is supplied into the blood flow route with filtration by the ultrafiltration unit withheld and the transmembrane pressure difference occurring when the patient's blood is supplied into the blood flow route with the filtration by the ultrafiltration unit withheld;
a plasma-total-protein-acquiring unit that acquires a plasma total protein or a correlation value of plasma total protein with reference to the colloid osmotic pressure or the correlation value of colloid osmotic pressure acquired by the colloid-osmotic-pressure-acquiring unit; and
a control unit that executes:
a first step in which the liquid that does not generate colloid osmotic pressure is supplied into the blood flow route with the filtration by the ultrafiltration unit withheld, and the transmembrane pressure difference is calculated by using the detecting unit; and
a second step in which the patient's blood is supplied into the blood flow route with the filtration by the ultrafiltration unit withheld, and the transmembrane pressure difference is calculated by using the detecting unit,
wherein the blood pump and a duplex pump are stopped to stop flow or liquid in the blood flow route and in the dialysate flow route;

wherein the second step is performed while the blood pump and the duplex pump are stopped, on a condition that a predetermined time has lapsed since a start of a treatment in a treatment step;

wherein the colloid-osmotic-pressure-acquiring unit acquires the colloid osmotic pressure or the correlation value of colloid osmotic pressure with reference to the transmembrane pressure difference calculated in the first step and the transmembrane pressure difference calculated in the second step;

wherein the blood pump and the dialysate pump are stopped, on a condition that a predetermined time has lapsed since a start of a treatment in a treatment step and the patient's blood is supplied to the blood flow route by the ultrafiltration unit;

wherein the plasma total protein or the correlation value of plasma total protein stored in a storage unit or transmitted to a server is linked to pieces of patient information;

wherein the control unit is capable of sequentially executing a priming step in which a priming solution is supplied into the blood circuit and the treatment step in which blood purification treatment is performed with the blood purifier while the patient's blood is caused to extracorporeally circulate through the blood circuit; and wherein the liquid that does not generate colloid osmotic pressure and is supplied into the blood flow route in the first step is the priming solution that is used in the priming step; and the patient's blood that is supplied into the blood flow route in the second step is the patient's blood that is caused to extracorporeally circulate in the treatment step.

2. The blood purification apparatus according to claim 1, wherein the detecting unit includes a blood-flow-route-side inlet-pressure-detecting unit that detects a blood pressure on an inlet side with respect to the blood flow route of the blood purifier; a blood-flow-route-side outlet-pressure-detecting unit that detects a blood pressure on an outlet side with respect to the blood flow route; a dialysate-flow-route-side inlet-pressure-detecting unit that detects a dialysate pressure on an inlet side with respect to the dialysate flow route of the blood purifier; and a dialysate-flow-route-side outlet-pressure-detecting unit that detects a dialysate pressure on an outlet side with respect to the dialysate flow route.

3. The blood purification apparatus according to claim 1, wherein the detecting unit is provided at a predetermined position; the transmembrane pressure difference occurring when the liquid that does not generate colloid osmotic pressure is supplied into the blood flow route with the filtration by the ultrafiltration unit withheld is storable as a theoretical value; and the colloid-osmotic-pressure-acquiring unit acquires the colloid osmotic pressure of the patient's blood in the blood flow route or the correlation value of colloid osmotic pressure with reference to the theoretical value and the transmembrane pressure difference occurring when the patient's blood is supplied into the blood flow route with the filtration by the ultrafiltration unit withheld.

4. The blood purification apparatus according to claim 1, wherein the plasma total protein or the correlation value of plasma total protein provide an estimation of a patient's state of nutrition.

5. The blood purification apparatus according to claim 4, further comprising:
a display that displays the plasma total protein or the correlation value of the plasma total protein.

6. The blood purification apparatus according to claim 1, further comprising:
a plurality of detecting units that detect a first transmembrane pressure difference when electromagnetic valves are closed and the plurality of detecting units detect a second transmembrane pressure difference when the electromagnetic valves are open so that the transmembrane pressure difference is acquired.

7. The blood purification apparatus according to claim 1, wherein the dialysate pump is a duplex pump.

8. A method of estimating a patient's state of nutrition on a blood purification apparatus, the blood purification apparatus including
a blood circuit including an arterial blood circuit and a venous blood circuit and that allows a patient's blood to extracorporeally circulate from a distal end of the arterial blood circuit to a distal end of the venous blood circuit;
a blood purifier provided between the arterial blood circuit and the venous blood circuit and that purifies the patient's blood flowing through the blood circuit, the blood purifier having a blood flow route through which the patient's blood extracorporeally circulating through the blood circuit flows and a dialysate flow route through which dialysate flows, the blood flow route and the dialysate flow route being separated from each other by a blood purification membrane for purifying the patient's blood;
an ultrafiltration unit that performs ultrafiltration by filtering out water from the patient's blood in the blood flow route through the blood purification membrane and draining the water through the dialysate flow route;
a blood pump;
a dialysate pump; and
detecting with a detecting unit a transmembrane pressure difference occurring on the blood purification membrane under a pressure difference between liquid in the blood flow route and liquid in the dialysate flow route;
acquiring a colloid osmotic pressure of the patient's blood in the blood flow route or a correlation value of colloid osmotic pressure with reference to the transmembrane pressure difference occurring when liquid that does not generate colloid osmotic pressure is supplied into the blood flow route with filtration by the ultrafiltration unit withheld and the transmembrane pressure difference occurring when the patient's blood is supplied into the blood flow route with the filtration by the ultrafiltration unit withheld;
acquiring a plasma total protein or a correlation value of plasma total protein with reference to an acquired colloid osmotic pressure or an acquired correlation value of colloid osmotic pressure;
executing with a control unit:
a first step in which the liquid that does not generate colloid osmotic pressure is supplied into the blood flow route with the filtration by the ultrafiltration unit withheld, and the transmembrane pressure difference is calculated by using the detecting unit; and
a second step in which the patient's blood is supplied into the blood flow route with the filtration by the ultrafiltration unit withheld, and the transmembrane pressure difference is calculated by using the detecting unit,
stopping the blood pump and a duplex pump to stop flow or liquid in the blood flow route and in the dialysate flow route;

performing the second step while the blood pump and the duplex pump are stopped, on a condition that a predetermined time has lapsed since a start of a treatment in a treatment step;

calculating a transmembrane pressure difference between the first step and the transmembrane pressure difference in the second step;

sequentially executing a priming step in which a priming solution is supplied into the blood circuit and the treatment step in which blood purification treatment is performed with the blood purifier while the patient's blood is caused to extracorporeally circulate through the blood circuit;

supplying the liquid that does not generate colloid osmotic pressure into the blood flow route in the first step as a priming solution in the priming step; and supplying the patient's blood into the blood flow route from the second step that is extracorporeally circulated in the treatment step;

wherein the plasma total protein or the correlation value of plasma total protein stored in a storage unit or transmitted to a server is linked to pieces of patient information.

9. The method of estimating a patient's state of nutrition on a blood purification apparatus according to claim 8, wherein the detecting unit includes a blood-flow-route-side inlet-pressure-detecting unit that detects a blood pressure on an inlet side with respect to the blood flow route of the blood purifier; a blood-flow-route-side outlet-pressure-detecting unit that detects a blood pressure on an outlet side with respect to the blood flow route; a dialysate-flow-route-side inlet-pressure-detecting unit that detects a dialysate pressure on an inlet side with respect to the dialysate flow route of the blood purifier; and a dialysate-flow-route-side outlet-pressure-detecting unit that detects a dialysate pressure on an outlet side with respect to the dialysate flow route.

10. The method of estimating a patient's state of nutrition on a blood purification apparatus according to claim 8, wherein the detecting unit is provided at a predetermined position; the transmembrane pressure difference occurring when the liquid that does not generate colloid osmotic pressure is supplied into the blood flow route with the filtration by the ultrafiltration unit withheld is stored as a theoretical value; and the colloid osmotic pressure of the patient's blood in the blood flow route or the correlation value of colloid osmotic pressure is acquired with reference to the theoretical value and the transmembrane pressure difference occurring when the patient's blood is supplied into the blood flow route with the filtration by the ultrafiltration unit withheld.

11. The method of estimating a patient's state of nutrition on a blood purification apparatus according to claim 8, further comprising estimating the patient's state of nutrition based on the plasma total protein or the correlation value of the plasma total protein.

12. The method of estimating a patient's state of nutrition on a blood purification apparatus according to claim 11, further comprising:

displaying the plasma total protein or the correlation value of the plasma total protein.

13. The method of estimating a patient's state of nutrition on a blood purification apparatus according to claim 8, further comprising:

closing electromagnetic valves and detecting a first transmembrane pressure difference with a plurality of detecting units;

opening the electromagnetic valves and detecting a second transmembrane pressure difference with the plurality of detecting units; and acquiring the transmembrane pressure difference by subtracting the first transmembrane pressure difference from the second transmembrane pressure difference.

14. The method according to claim 8, wherein the dialysate pump is a duplex pump.

* * * * *